United States Patent [19]

Wells, Jr.

[11] Plant 4,760

[45] Aug. 25, 1981

[54] MINIATURE ROSE PLANT

[76] Inventor: Verlie W. Wells, Jr., P.O. Box 157, Brighton, Tenn. 18011

[21] Appl. No.: 81,135

[22] Filed: Oct. 2, 1979

[51] Int. Cl.[3] ..... A01H 5/00
[52] U.S. Cl. ..... Plt./7
[58] Field of Search ..... Plt./7

*Primary Examiner*—Robert E. Bagwill
*Attorney, Agent, or Firm*—Mason, Mason and Albright

[57] ABSTRACT

A novel miniature rose variety characterized by its double blossoms of sixty to seventy symmetrically arranged petals which remain relatively tight at maturity and are of satiny medium intense red color, the petals having a white creamy white base.

1 Drawing Figure

SUMMARY OF THE INVENTION

The present invention relates to a new and distinct variety of hardy, disease-resistant rose plant of the miniature class; the variety being primarily characterized by the exhibition quality and relatively large size of its double blooms having sixty to seventy petals symmetrically arranged, such petals remaining relatively tight at maturity and being of a satiny medium intense red color with the petals having a white creamy white base.

DETAILED DESCRIPTION OF THE INVENTION

The variety is further characterized by:

Its flowers borne singly to stem and clusters of five blooms;

A very light penetrating tea-type fragrance;

A desirable bloom form and growth habits with a strong peduncle, straight stem, upright sepals and single bloom characteristics.

The plant, which has a normal height of fourteen to sixteen inches, which is reasonably tall for miniature, is hardy and grows in bush form both in greenhouses and outdoors. It may be used to good effect for garden decoration and to provide exhibition blooms.

The present variety of miniature rose was originated by me in my nursery in Brighton, Tenn. as a cross between a Judy Fisher (miniature) as a seed parent which was selected because of the plant's good bloom form and growth habit. The pollen parent was an unknown seedling having an excellent bloom form and foliage.

Subsequent to the origination of the variety, I have successfully asexually reproduced it in my nursery located as aforesaid by budding as well as by cutting, the reproduction having run true in all respects.

The color photograph illustrates the variety, including the foliage, buds and flowers and illustrating also in a divided bloom the white to creamy white base. Referring now specifically to the new and distinct variety of miniature rose plant, the following terminology being in accordance with the American Rose Society's basic color groups and other indications of ordinary dictionary significance.

Type: Hardy, dwarf, bushy; tall (14 to 16 inches) for a miniature; greenhouse; outdoors; cut flowers; garden decorations; potted plant.

Class: Miniature. Variety name "Elvis."

Flowers:

*Continuity.*—Continuous — repeat bloom all season.

*Fragrance.*—Very light penetrating; tea.

*Flowers borne.*—Singly to stem and clusters of five blooms on upright, well-branched, strong stems.

*Quantity of bloom.*—Freely, both indoor and outdoor garden and greenhouse.

Bud:

*Peduncle.*—Strong upright; curved upward; light green; thorns average; prickles and hairs — none.

*Before calyx breaks.*—Size — medium for miniature; Form: tall approximately ½ inch, ovoid, sepals upright on strong, straight peduncle. Color: light green.

*As calyx breaks.*—Color — medium red, more intensive when grown outdoors; opened: same color. Size: small.

Bloom:

*Size when fully opened.*—Small average about one inch in diameter when fully opened. Petalage very double with sixty to seventy petals arranged very symmetrically: Form — full, tightly rolled outward. Petals: Medium thickness with satiny surface on both inside and outside.

*Shape.*—Full, tightly rolled outward; point at center, remaining tight at maturity, rolled outward.

*Color.*—Newly opened flower from a plant grown outdoors, July, 1979, Memphis, Tenn.

Classification according to American Rose Society basic color groups is Group No. 14. Red blend. Primarily red but tones of other hues with shading to near white or creamy at base. Petal color: medium red tip on upper surface fading through approximately equal light red and still lighter red bands to a white or creamy base. The lower petal surface has a similar white base and bands of light reds splashed and streaked with white and lighter red similar to the upper surface except the latter is less broad. The petal's surface on the inside base is white to creamy white, and on the outside of the petal is white to creamy white except a top edge of medium red. Under the Royal Horticultural Colour Chart, the red in the petal is Turkey Red 46-C and the white is 155-C. Between the red and white, the predominant bands are rhodonite 51A for the light red next to the medium red and neyron 55C for the lighter red next to the white.

Reproductive organs:

*Stamens.*—Antlers: Many, three-layered small, arranged regularly around pistil, color: yellow.

*Filaments.*—Medium short; yellow at top, center; Color: red at base turns to light green.

*Pollen.*—Large amount; color — golden yellow.

*Styles.*—Branched, loosely separated, uneven length, medium length; heavy.

*Stigma.*—Yellow, turning to bright red.

*Ovaries.*—All enclosed in calyx.

*Hips and fruit.*—None with own pollen.

*Sepals.*—Caducous (soon falling), curled, spear-shaped.

*Seed.*—None.

Foliage:

*Leaves.*—Compound of five (sometimes 3 or 7) leaflets; abundant; medium-small; leathery, glossy. Color: new foliage, upper side, bronzy to purple red; lower side, bronzy to medium green; old foliage, upper side, leathery, glossy dark green; lower side, medium green.

*Leaflets.*—Shape: ovoid pointed; margin even serrated, smooth ribs, light veins, impressed. Leaf-stems: red upper side; light green, lower side, with prickles. Stipitate long, pointed and spiraled.

Growth:

*Habit.*—Dwarf, medium-compact.

*Growth.*—Free, vigorous, upright, well-branched.

*Canes.*—Medium, sturdy.

*Main stems.*—Medium-size; color, light green.

*Thorns.*—Average number — (3 to 4 per 10 cm. of main stem); fairly long, nearly straight; color: red at point, tapering to light brown.

*Prickles and hairs.*—None.

*Branches.*—Sturdy, curved upward. Color: light green; thorns average;

*New shoots.*—Color: Bronze to purple-red, turning to leathery, glossy dark green.

The miniature rose plant and its flowers as herein described may vary in slight detail due to climatic, soil and cultural conditions under which a variety may be grown; the present description being of the variety as grown in Memphis, Tenn.

The following is claimed:

1. A new and distinct variety of miniature rose plant which is hardy, dwarf, medium-compact, well-branched and bushy, essentially as illustrated and described, characterized by buds and flowers which are double with from sixty to seventy petals arranged very symmetrically in a full, tightly rolled outwardly form with points at the center and remaining tightly rolled outwardly form with points at the center and remaining tight at maturity, being of medium red on upper edge of inside petal with an inside base of white to creamy white; and further characterized by the plant being hardy, reasonably tall for a miniature, and having good growth habits and disease-resistant foliage.

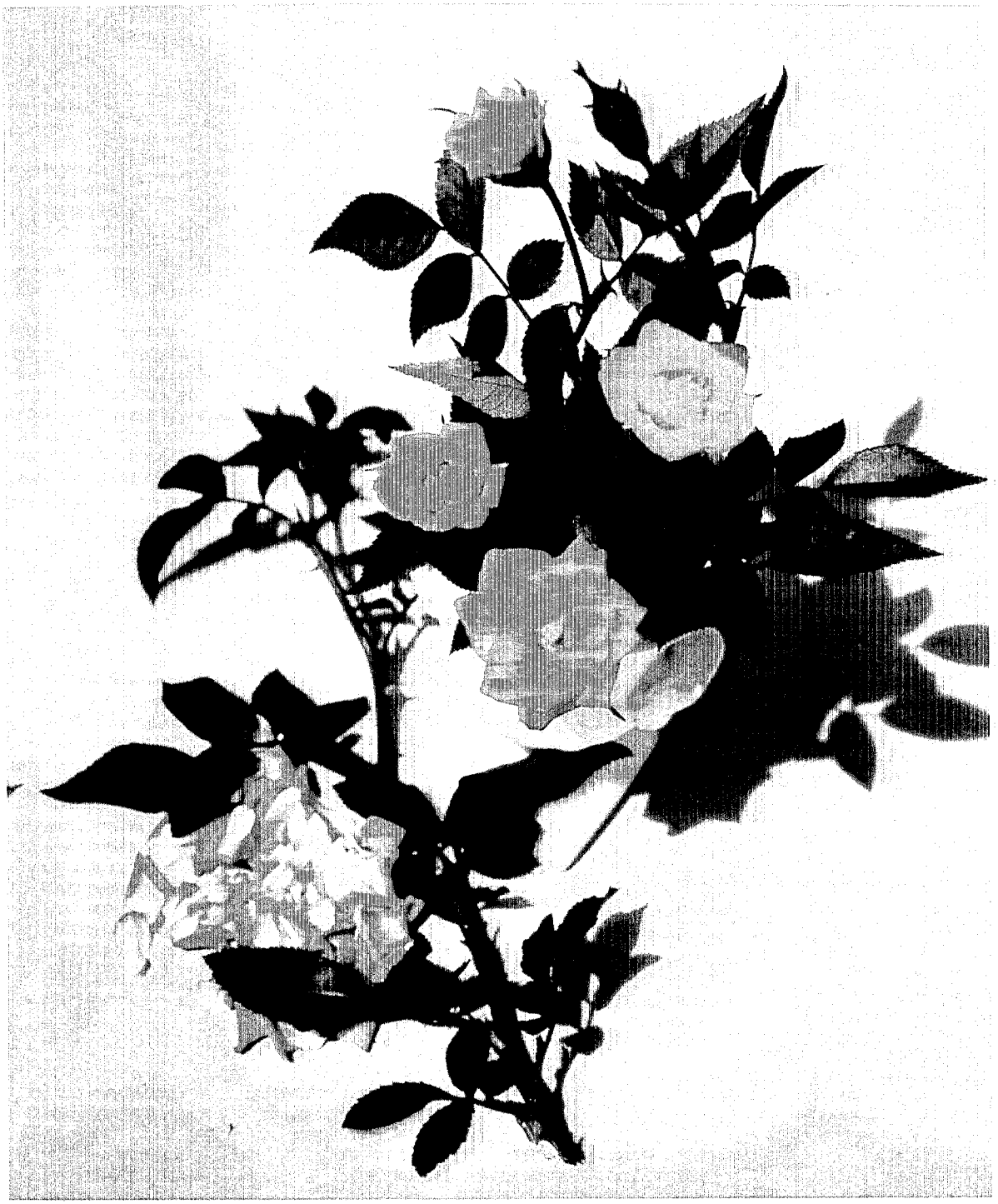

* * * * *